US010350070B2

(12) United States Patent
Elist

(10) Patent No.: US 10,350,070 B2
(45) Date of Patent: *Jul. 16, 2019

(54) PROSTHESIS FOR IMPROVED PENIS FUNCTION

(71) Applicant: Menova International, Inc., Beverly Hills, CA (US)

(72) Inventor: James Elist, Beverly Hills, CA (US)

(73) Assignee: Menova International, Inc., Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/905,652

(22) PCT Filed: Mar. 4, 2016

(86) PCT No.: PCT/US2016/020881
§ 371 (c)(1),
(2) Date: Feb. 26, 2018

(87) PCT Pub. No.: WO2017/116489
PCT Pub. Date: Jul. 6, 2017

(65) Prior Publication Data
US 2018/0214272 A1    Aug. 2, 2018

(51) Int. Cl.
*A61F 5/00* (2006.01)
*A61F 2/26* (2006.01)

(52) U.S. Cl.
CPC ..................................... *A61F 2/26* (2013.01)

(58) Field of Classification Search
CPC ................. A61F 2/26; A61F 2/02; A61F 2/04
USPC ............................... 600/38–41; 128/DIG. 25
See application file for complete search history.

(56) References Cited

U.S. PATENT DOCUMENTS

| 4,204,530 | A | 5/1980 | Finney |
| 4,523,584 | A | 6/1985 | Yachia |
| 4,602,625 | A | 7/1986 | Yachia |
| 4,982,731 | A | 1/1991 | Lue |
| 6,015,380 | A | 1/2000 | Subrini |
| 6,475,137 | B1 | 11/2002 | Elist |
| 6,537,204 | B1 | 3/2003 | Elist |
| 9,504,573 | B1 * | 11/2016 | Elist ......................... A61F 2/26 |

FOREIGN PATENT DOCUMENTS

WO        2005/065598 A1    7/2005

* cited by examiner

*Primary Examiner* — John P Lacyk
(74) *Attorney, Agent, or Firm* — Patent Law & Venture Group, PLLC; Gene Scott

(57) ABSTRACT

A subcutaneous prosthesis subcutaneously implanted within a penis, the prosthesis forming two sides of an elongated cylinder, the sides hinged along top longitudinal edges of their sides. One end of the prosthesis has a gauze sheath providing a means to secure the prosthesis from moving relative to the corpora cavernosa around which it is placed. When the penis is erect it grows in girth thereby causing the two sides of the cylindrical prosthesis to spread divergently and forcing a press-rib against the deep dorsal vein of the penis, thereby restricting blood flow out of the penis so as to improve erectile rigidity and duration.

7 Claims, 5 Drawing Sheets

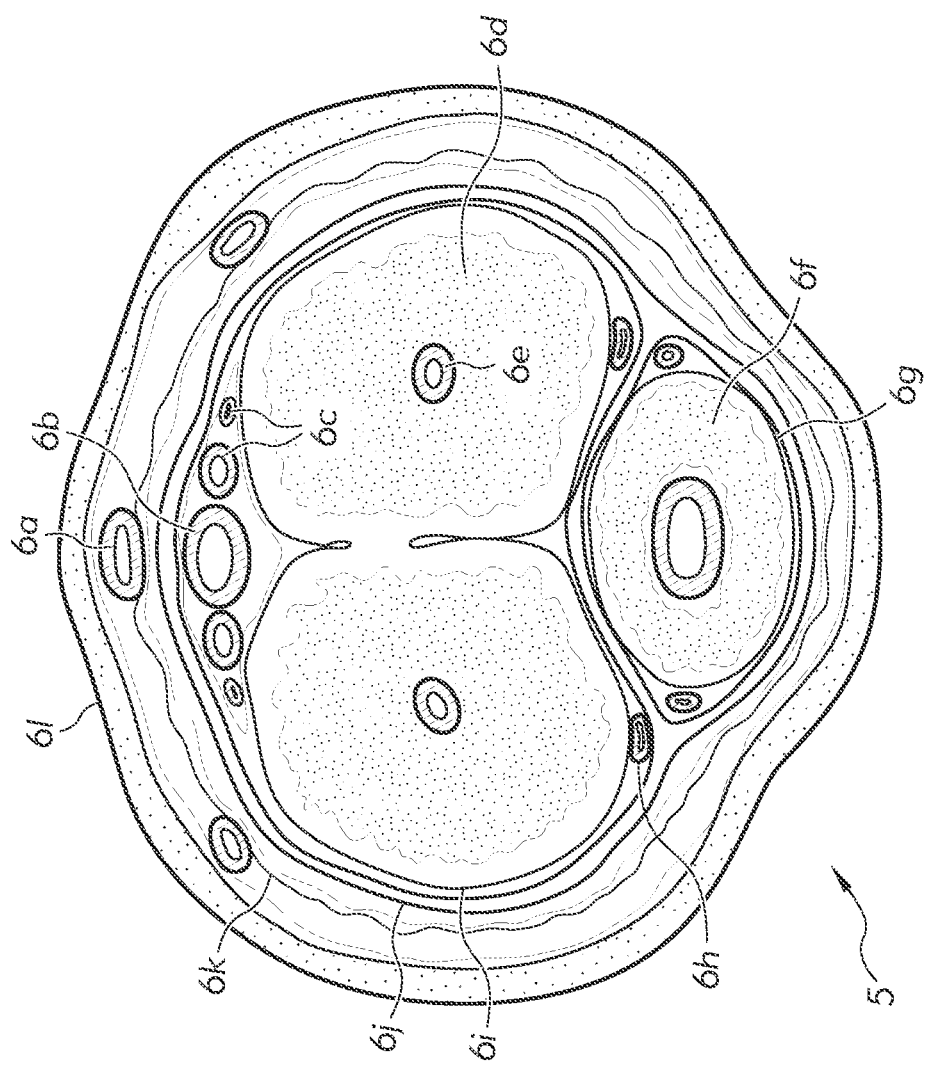

PROSTHESIS FOR IMPROVED PENIS FUNCTION

BACKGROUND OF THE INVENTION

Field of the Invention

This invention relates generally to surgical prostheses for the enhancement of appearance and operation of organs, and more particularly to a penile prosthesis enabling a damaged penis or poor penis function to be restored to a satisfactory sexual function.

Description of Related Art

A prosthesis for implantation into a penis to provide rigidity and improve dimensions is known in the art. Such a prosthesis may include an elongated, malleable rod portion which is housed within a generally tubular, physiologically inert plastic body. The malleable rod portion enables the prosthesis to conform to a variety of shapes by bending or twisting it. During intercourse the prosthesis will maintain the penis in an erect state, and afterwards the penis may be positioned and maintained in a more convenient and comfortable position. Finney, U.S. Pat. No. 4,204,530 describes a prosthesis with a sleeve for increasing the penile diameter, and which includes a flexible sheet of soft, physiologically acceptable material, the sheet being of sufficient length when formed in the general shape of a cylindrical sleeve to extend from the glans penis to the base of the penis and of a width which is insufficient to completely encircle the penis, but is sufficient to cover the corpora cavernosa. Improved rod-type penile prostheses may have a relatively stiff proximal portion for positioning inside the corpora cavernosa adjacent the pubis for supporting the prosthesis, a longer relatively stiff distal portion for positioning in the corpora cavernosa of the pendulous penis, and a hinge separating the distal and proximal portions. Masters, U.S. Pat. No. 4,669,456 describes a penile prosthesis which comprises an elastomeric rod and a metal wire coil coaxially imbedded within at least a portion of the rod. Subrini, U.S. Pat. No. 6,015,380 describes a prosthesis which can be used to increase penile volume. Moreira de Azeredo, WO 86/01398 describes a penile rigidity prosthesis for the treatment of erectile impotence in men including at least one penile prosthesis comprising an elongated malleable cylindrical body adapted to be surgically placed in the corpora cavernosa.

The prior art teaches the use of a subcutaneously placed prostheses to rigidize the penis, but does not teach the use of certain contours that provide structural advantages nor a means for restricting flow through the dorsal vein, or a means for preventing axial movement or sliding of the prosthesis relative to the penis' long axis. The present invention fulfills these needs and provides further related advantages as described in the following summary.

SUMMARY OF THE INVENTION

The present invention teaches certain benefits in construction and use which give rise to the following objectives. A penile prosthesis may have a cylindrical, elongated body providing a wall thickness varying circumferentially from a maximum thickness at its top surface, to a minimum thickness along its bottom surface. The wall thickness may further vary longitudinally from a maximum thickness at a proximal end of the device to a minimum thickness at a distal end. The apparatus is preferably made of silicone rubber and has a length and size enabling subcutaneous implantation around the corpora cavernosa providing sufficient rigidity for enabling coitus while still being flexible enough to be conveniently positioned when the penis is flaccid.

An objective of the described and claimed prosthesis is to provide rigidity to the human penis so as to enable coitus.

A further objective is to provide an appropriate tapered appearance.

A still further objective is to enable surgical implantation without removal of existing organ portions or related tissues.

A yet further objective is to prevent the prosthesis from moving axially after being implanted.

A further objective is to provide a means for anchoring the distal end of the prosthesis.

An important objective is to stem the flow of blood out of the penis during coitus.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 9 is a cross-sectional view of the human penis.

DETAILED DESCRIPTION OF THE INVENTION

Figure 1:
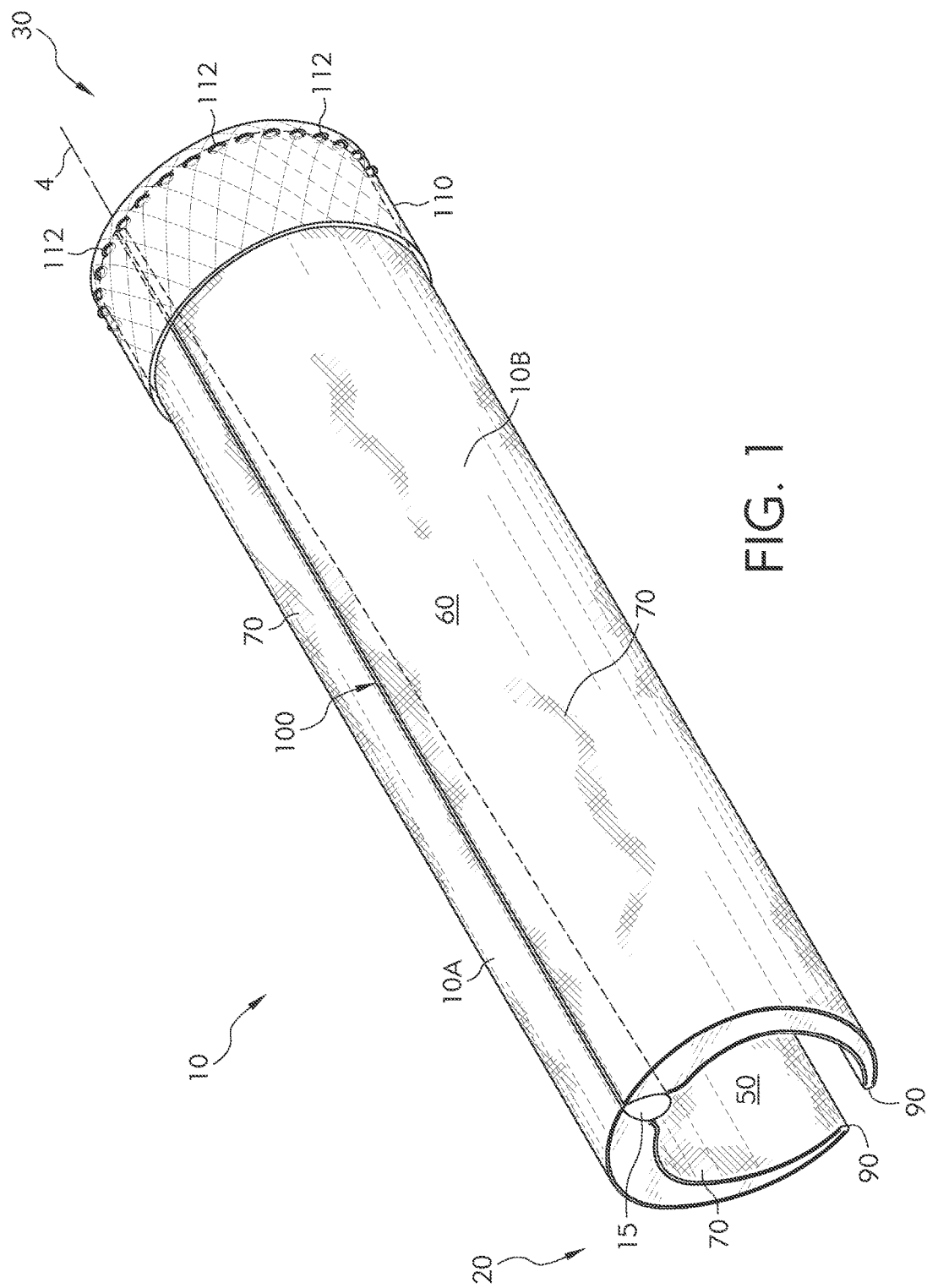
FIG. 1 is a perspective view of the described and illustrated prosthesis.

The above described drawing figures illustrate the invention in at least one of its preferred embodiments, which is further defined in detail in the following description.

The invention is a penile prosthesis, of silicone rubber or an equivalent material, which may be implanted subcutaneously in the human penis 5. FIG. 9 is a section illustrating the anatomy of penis 5 and showing in particular, the dorsal vein 6a, the deep dorsal vein 6b, the dorsal artery and nerve 6c, the corpus cavernosum penis 6d, the profunda artery 6e, the corpus spongiosum and urethra 6f, the tunica albuginea 6g, the intercavernous septum of buck's fascia 6h, the tunica albuginea of corpus caversosum penis 6i, the buck's fascia 6j, the dartos fascia 6k, and the skin 6l which is the outer layer of penis 5.

Figure 2:
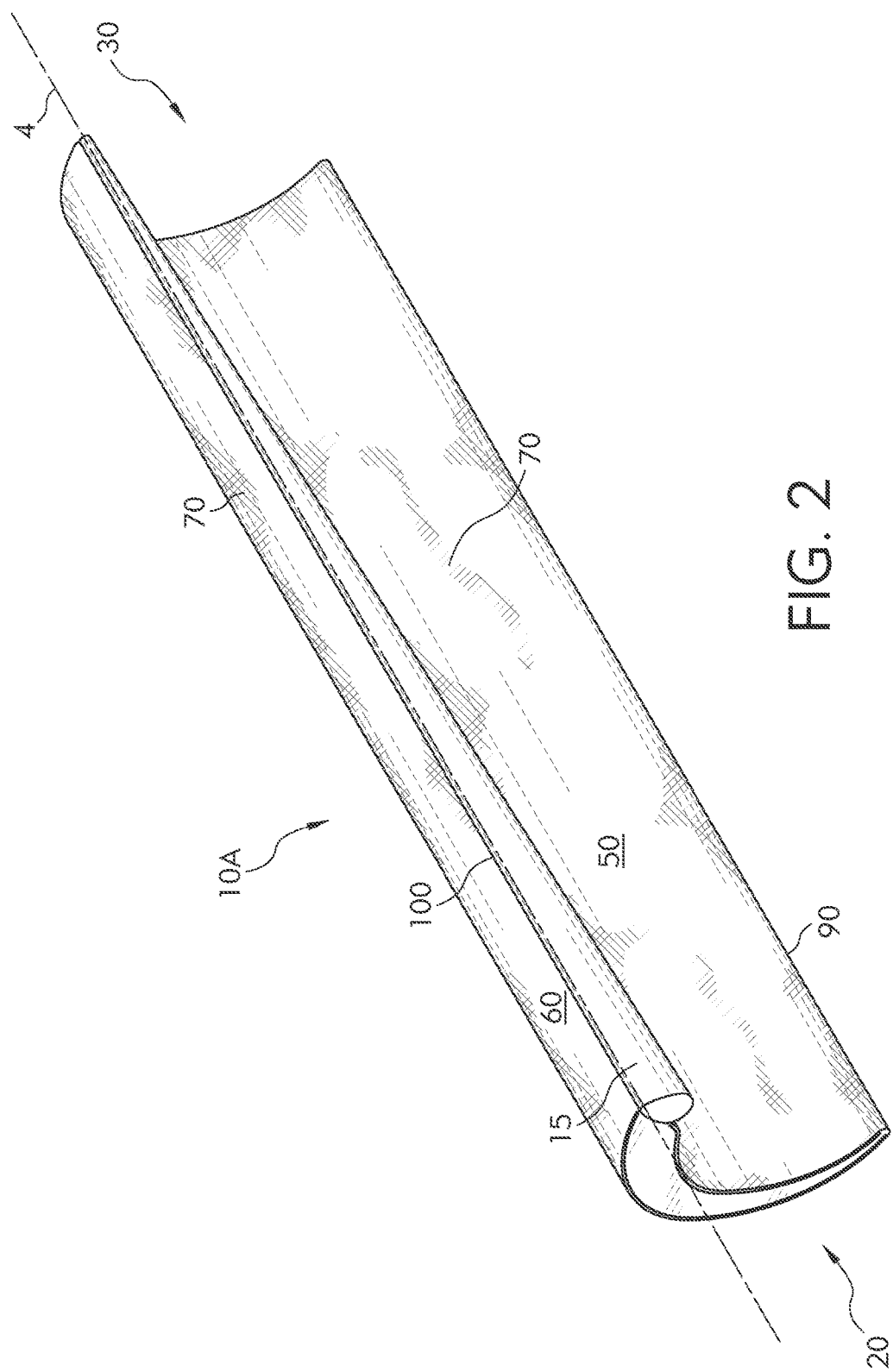
FIG. 2 is a perspective view of a left half thereof.

The prosthesis may have a cylindrical body 10 of a selected longitudinal length aligned with the long axis 4 of penis 5, and may be open at both its proximal end 20 (nearest to the testacies), as well as at its opposite distal end 30 (nearest to the glans penis) as shown in FIG. 1. Body 10 may have an inside surface 50 and an outside surface 60 and may be formed as a single integral part with two joined halves 10A, 10B or alternately it may be formed as two separate halves 10A, 10B which may be later joined together as shown in FIG. 1. Halves 10A, 10B may be mirror images of each other as shown and may be joined prior to or during implantation into penis 5. The prosthesis implantation process is taught in Finney, U.S. Pat. No. 4,202,530 which is hereby incorporated into the present application by reference. Thus, it is clear that the prosthesis can be formed to have a size and shape adapted for subcutaneous implantation below exterior skin 6*l* and adjacent to buck's fascia 6*h*. The prosthesis may extend from the base of penis 5 at its proximal end 20 to the glans penis (not shown) at distal end 30. Both inside surface 50 and outside surface 60 may have a silicon net sheeting 70 imbedded just under these surfaces as shown in FIGS. 1 and 2, wherein net sheeting 70 may extend continuously over and/or under both halves 10A, 10B and thus function as a hinge between the halves along joining line 100. Halves 10A and 10B may therefore move between the two attitudes shown in FIGS. 7 and 8. The prosthesis, when in place around buck's fascia 6*j*, may be anchored using sutures joining net sheeting 70 to buck's fascia 6*j* or to tunica albuginea 6*g*, or both.

As shown in FIGS. 1 and 2, a press-rib 15, of silicone rubber or equivalent material, may be joined to body 10 and, or to net sheeting 70, or both, along joining line 100. Press-rib 15 may extend only partially or fully over the length of body 10. The hardness of the material of press-rib 15 is selected to be effective in the compressing action shown in FIG. 8. The function of press-rib 15 will be discussed below in conjunction with descriptions of FIGS. 6-8.

Body 10 may have a wall thickness that varies circumferentially from a maximum thickness along joining line 100 in FIG. 1, to a minimum thickness along bottom edges 90. It should be clear that FIG. 1 represents body 10 when the two halves 10A, 10B are joined along joining line 100. The wall thickness of body 10 further may vary longitudinally from a maximum thickness at proximal end 20, to a minimum thickness at distal end 30. Edges 90 may be spaced apart as shown in FIGS. 1 and 6-8 and this gap may extend the full length of body 10.

The thicker wall at proximal end 20, when placed adjacent to the base of the penis provides the advantage of improved rigidity of the prosthesis, and the thinner wall at distal end 30, adjacent to the glans penis, allows for improved movement of the glans penis. The uniform taper from proximal end 20 to distal end 30 provides improved flexibility of the penis when flaccid. The thicker wall along joining line 100 provides greater structural strength where the highest compressive forces occur during coitus. The circumferential taper provides improved flexibility of the penis and a more natural penile conformation and appearance as well as improved blood flow in general since the prosthesis wall may be quite thin near the glans penis. The important overall result of the conformation of the prosthesis is that it uses a relatively small amount of material while achieving sufficient rigidity and blood flow. The use of net sheeting 70 provides a wide range of choices as to placement of sutures. The use of split halves 10A, and 10B facilitates implantation and provides the opportunity to use asymmetrical halves as may be necessary for repair of damaged or misshaped organs. The space between the bottom longitudinal edges 90 allows the penis to expand without restraint, see FIG. 8.

Figure 6:
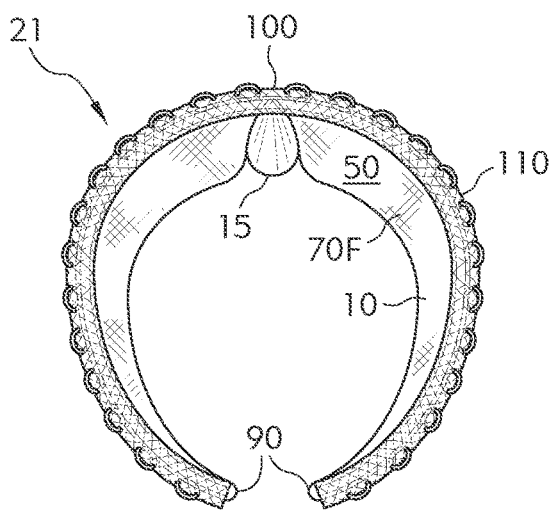
FIG. 6 is a distal elevation view thereof.
Figure 7:
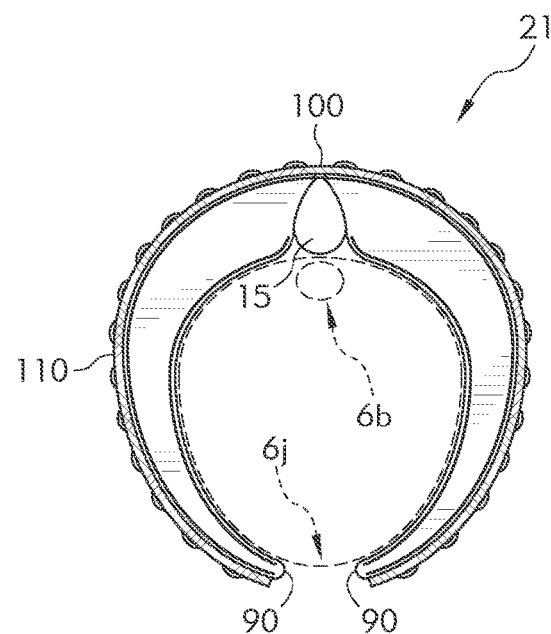
FIG. 7 is a proximal elevation view thereof shown with a flaccid penis.

The interior space within body 10 is preferably oblate, as is the human penis 5 with height greater than width as shown in FIGS. 6 and 7 with a preferred ratio of height to width of approximately 1.12. It has been found that this form enables improved blood flow as well as a more comfortable fit to the shape of the penis.

Figure 3:
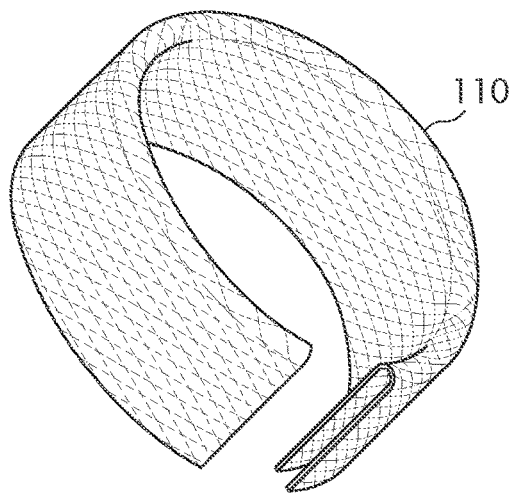
FIG. 3 is a perspective view of a gauze sheath thereof.
Figure 4:
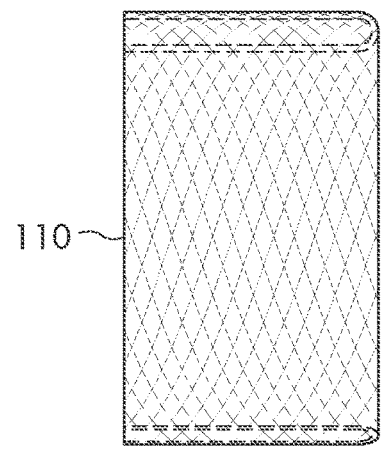
FIG. 4 is a side elevation view thereof.
Figure 5:
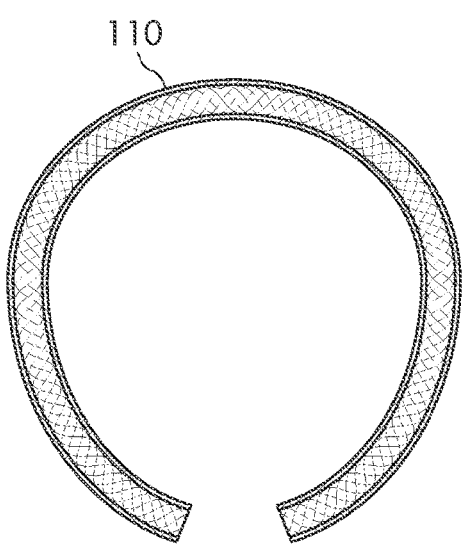
FIG. 5 is a rear elevation view thereof.

As shown in FIG. 1, body 10 may be fitted with a gauze sheath 110 at distal end 30 and it may be fixed thereto by sutures 112 as also shown. FIGS. 3-5 show that gauze sheath 110 may have the same shape as the distal end 30 of body 10 so that gauze sheath 110 may be fitted up against the terminal edge of distal end 30 and may lay against both inner surface 50 as well as outer surface 60 of body 10 so that it does not produce a bulky area adjacent to the glans penis and provides an improved implantation. Gauze sheath 110 provides a functional means for suturing the distal end 30 of body 10 to the buck's fascia 6*h* so that body 10 is unable to move longitudinally.

Figure 8:
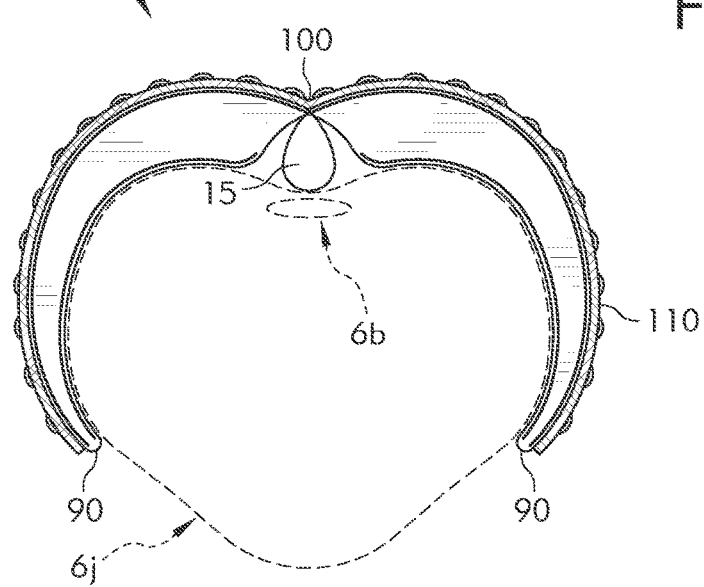
FIG. 8 is a further proximal elevation view thereof shown with engorged penis.

FIG. 6 shows the prosthesis as viewed from the distal end 30 looking toward the proximal end 20 while FIGS. 7 and 8 show the prosthesis as viewed from the proximal end 20 looking toward the distal end 30 and additionally show buck's fascia 6*h* in dashed outline. Skin 6*l* is not shown in FIG. 6, 7, or 8. Deep dorsal vein 6*b* is shown located at the 12 o'clock position (under joining line 100) in FIGS. 7 and 8, whereas FIG. 7 represents a flaccid penis 5 while FIG. 8 represents an erect or engorged penis 5. It is shown that press-rib 15 compresses deep dorsal vein 6*b* to slow outward blood flow during the erection process and in order to maintain the erect condition.

While the invention has been described with reference to at least one preferred embodiment, it is to be clearly understood by those skilled in the art that the invention is not limited thereto. Rather, the scope of the invention is to be interpreted only in conjunction with the appended claims

What is claimed is:

1. A penile prosthesis comprising:
   a cylindrical body for subcutaneous implantation into a penis;
   said cylindrical body having two hingably-joined halves capable of mutually converging and mutually diverging depending on an erectile state of said penis; and
   further comprising a first gauze sheath sutured to an end of said cylindrical body in a position enabling suturing of said cylindrical body to a corpora cavernosum of said penis.

2. The penile prosthesis of claim 1 wherein said hingably-joined halves are joined by a second gauze sheet extensive on at least one of top surfaces and bottom surfaces of said hingably-joined halves.

3. The penile prosthesis of claim 1 wherein said cylindrical body is formed as a single integral part having a length for extending over at least a portion of a length of a penis.

4. The penile prosthesis of claim 1 wherein said cylindrical body has a wall thickness varying circumferentially from a maximum thickness to a minimum thickness.

5. The penile prosthesis of claim 1 wherein said cylindrical body has a wall thickness varying longitudinally from a maximum thickness to a minimum thickness.

6. The penile prosthesis of claim 1 wherein said cylindrical body has two opposing longitudinal edges defining a longitudinal gap in said cylindrical body.

7. The penile prosthesis of claim 1 wherein said cylindrical body defines an oblate space therein.

* * * * *